(12) United States Patent
Prior

(10) Patent No.: US 11,134,931 B2
(45) Date of Patent: Oct. 5, 2021

(54) TISSUE SPECIMEN RETRIEVAL BAGS, DEVICES, AND SYSTEMS

(71) Applicant: COVIDIEN LP, Mansfield, MA (US)

(72) Inventor: Scott J. Prior, Shelton, CT (US)

(73) Assignee: Covidien LP, Mansfield, MA (US)

( * ) Notice: Subject to any disclaimer, the term of this patent is extended or adjusted under 35 U.S.C. 154(b) by 272 days.

(21) Appl. No.: 16/391,408

(22) Filed: Apr. 23, 2019

(65) Prior Publication Data

US 2019/0336117 A1 Nov. 7, 2019

Related U.S. Application Data

(60) Provisional application No. 62/665,010, filed on May 1, 2018.

(51) Int. Cl.
*A61B 17/00* (2006.01)

(52) U.S. Cl.
CPC .......... *A61B 17/00234* (2013.01); *A61B 2017/00287* (2013.01); *A61B 2017/00424* (2013.01); *A61B 2017/00438* (2013.01)

(58) Field of Classification Search
CPC ........ A61B 17/00234; A61B 17/32056; A61B 17/0218; A61B 17/221; A61B 2017/00287; A61B 2017/00438; A61B 2017/00424; A61B 2017/00358; A61B 2017/0225
See application file for complete search history.

(56) References Cited

U.S. PATENT DOCUMENTS

| | | | |
|---|---|---|---|
| 6,228,095 B1 | 5/2001 | Dennis | |
| 7,762,959 B2 | 7/2010 | Bilsbury | |
| 8,419,749 B2 | 4/2013 | Shelton, IV et al. | |
| 2004/0158261 A1 | 8/2004 | Vu | |
| 2014/0236168 A1 | 8/2014 | Shibley et al. | |
| 2017/0049427 A1 | 2/2017 | Do et al. | |
| 2018/0199961 A1* | 7/2018 | Prior | A61B 17/42 |

* cited by examiner

*Primary Examiner* — Melanie R Tyson
(74) *Attorney, Agent, or Firm* — Carter, DeLuca & Farrell LLP

(57) ABSTRACT

A tissue specimen retrieval device includes a housing, an outer shaft extending distally from the housing, an end effector assembly extending distally from the outer shaft in a deployed position, a tissue specimen bag supported on the end effector assembly and including an open end extending between proximal and distal end portions of the end effector assembly, a cinch loop disposed about the open end of the tissue specimen bag, and a distal cinch tab. The distal cinch tab is disposed at the distal end portion of the end effector assembly and extends from the open end of the tissue specimen bag. The distal cinch tab is operably coupled to the cinch loop such that pulling the distal cinch tab distally relative to the cinch loop constricts the cinch loop about the open end of the tissue specimen bag to cinch the open end of the tissue specimen bag closed.

10 Claims, 7 Drawing Sheets

TISSUE SPECIMEN RETRIEVAL BAGS, DEVICES, AND SYSTEMS

CROSS-REFERENCE TO RELATED APPLICATIONS

This application claims the benefit of and priority to U.S. Provisional Patent Application No. 62/665,010, filed on May 1, 2018, the entire contents of which are hereby incorporated herein by reference.

BACKGROUND

Technical Field

The present disclosure relates to tissue specimen retrieval from an internal body cavity and, more particularly, to tissue specimen retrieval bags, devices, and systems to facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment.

SUMMARY

The present disclosure provides tissue specimen retrieval bags, devices, and systems to facilitate retrieval of the tissue specimen from an internal body cavity. These and other aspects and features of the present disclosure are detailed below. As used herein, the term "distal" refers to the portion that is described which is further from a user, while the term "proximal" refers to the portion that is being described which is closer to a user. Further, any or all of the aspects and features described herein, to the extent consistent, may be used in conjunction with any or all of the other aspects and features described herein.

Provided in accordance with aspects of the present disclosure is a tissue specimen retrieval device including a housing, an outer shaft extending distally from the housing, an end effector assembly extending distally from the outer shaft in a deployed position thereof, a tissue specimen bag supported on the end effector assembly, a cinch loop, and a distal cinch tab. The end effector assembly defines a proximal end portion positioned adjacent a distal end portion of the outer shaft in the deployed position and a distal end portion distally-spaced from the distal end portion of the outer shaft in the deployed position. The tissue specimen bag includes an open end extending between the proximal and distal end portions of the end effector assembly. The cinch loop is disposed about the open end of the tissue specimen bag. The distal cinch tab is disposed at the distal end portion of the end effector assembly and extends from the open end of the tissue specimen bag. The distal cinch tab is operably coupled to the cinch loop such that pulling the distal cinch tab distally relative to the cinch loop constricts the cinch loop about the open end of the tissue specimen bag to cinch the open end of the tissue specimen bag closed.

In an aspect of the present disclosure, the distal cinch tab is operably coupled to the cinch loop via a slip knot.

In another aspect of the present disclosure, an elongated tether is coupled to the tissue specimen bag towards the proximal end portion of the end effector assembly. In aspects, the elongated tether extends proximally through outer shaft and housing to a finger ring.

In still another aspect of the present disclosure, the end effector assembly is selectively deployable relative to the outer shaft from a retracted position, wherein the end effector assembly is disposed within the outer shaft, to the deployed position.

In yet another aspect of the present disclosure, an articulation mechanism is operably associated with the end effector assembly and configured to articulate the end effector assembly relative to the outer shaft.

In still yet another aspect of the present disclosure, the tissue specimen bag defines first and second channels each extending about a portion of the circumference of the open end of the tissue specimen bag. In such aspects, the end effector assembly may include first and second arms configured to extend at least partially through the first and second channels, respectively. Additionally or alternatively, distal ends of the first and second channels oppose and may be spaced-apart from one another with the distal cinch tab disposed therebetween.

In another aspect of the present disclosure, the cinch loop extends through the first and second channels.

Another tissue specimen retrieval device provided in accordance with aspects of the present disclosure includes a housing, an outer shaft extending distally from the housing, an end effector assembly extending distally from the outer shaft in a deployed position thereof, a tissue specimen bag supported on the end effector assembly, and a slack ring. The tissue specimen bag defines an open end and elongated body extending from the open end. The elongated body is folded back on itself at least once to define at least two folded layers. The slack ring is releasably disposed about the at least two folded layers of the elongated body of the tissue specimen bag.

In an aspect of the present disclosure, the end effector assembly is selectively deployable relative to the outer shaft from a retracted position, wherein the end effector assembly is disposed within the outer shaft, to the deployed position. In such aspects, the slack ring may be disposed about the at least two folded layers of the elongated body of the tissue specimen bag in the retracted position of the end effector assembly. Alternatively, the slack ring may be disposed about the at least two folded layers of the elongated body of the tissue specimen bag after the end effector assembly is deployed to the deployed position.

In another aspect of the present disclosure, an articulation mechanism is operably associated with the end effector assembly and configured to articulate the end effector assembly relative to the outer shaft.

In still another aspect of the present disclosure, the slack ring includes a ring body and a grasping tab extending from the ring body. The ring body may be resiliently flexible and/or the grasping tab may be is configured to facilitate removal of the slack ring from about the at least two folded layers of the elongated body of the tissue specimen bag.

In yet another aspect of the present disclosure, a cinch loop is disposed about the open end of the tissue specimen bag.

Also provided in accordance with aspects of the present disclosure are stand-alone tissue specimen bags including a cinch assembly and/or a slack ring. That is, the stand-alone tissue specimen bags of the present disclosure are similar to any of the aspects detailed herein except that such are stand-alone rather than being provided for use in conjunction with a retrieval device.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

The present disclosure provides tissue specimen retrieval bags, devices, and systems to facilitate retrieval of tissue from an internal body cavity.

Figure 1:
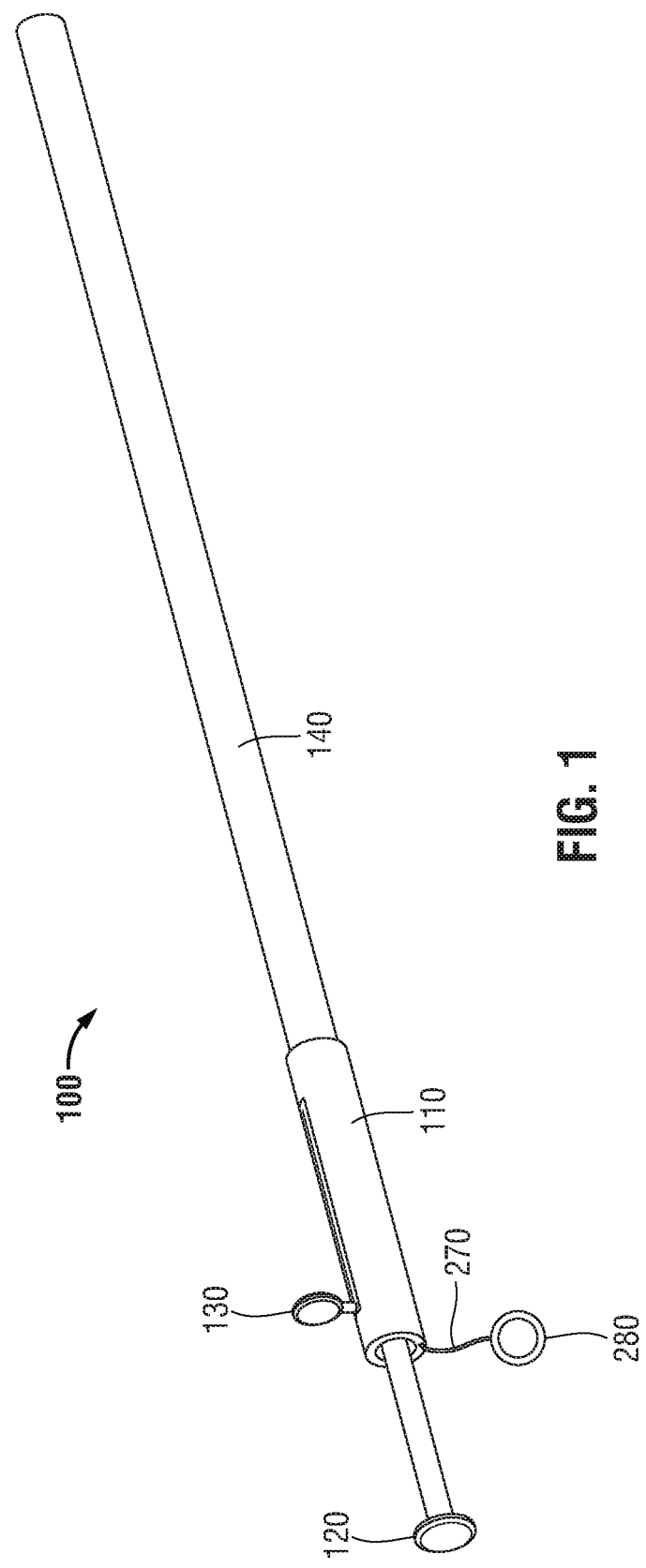
FIG. 1 is a side, perspective view of a tissue specimen retrieval device provided in accordance with aspects of the present disclosure, wherein an end effector assembly of the tissue specimen retrieval device is disposed in a retracted position.
Figure 2:
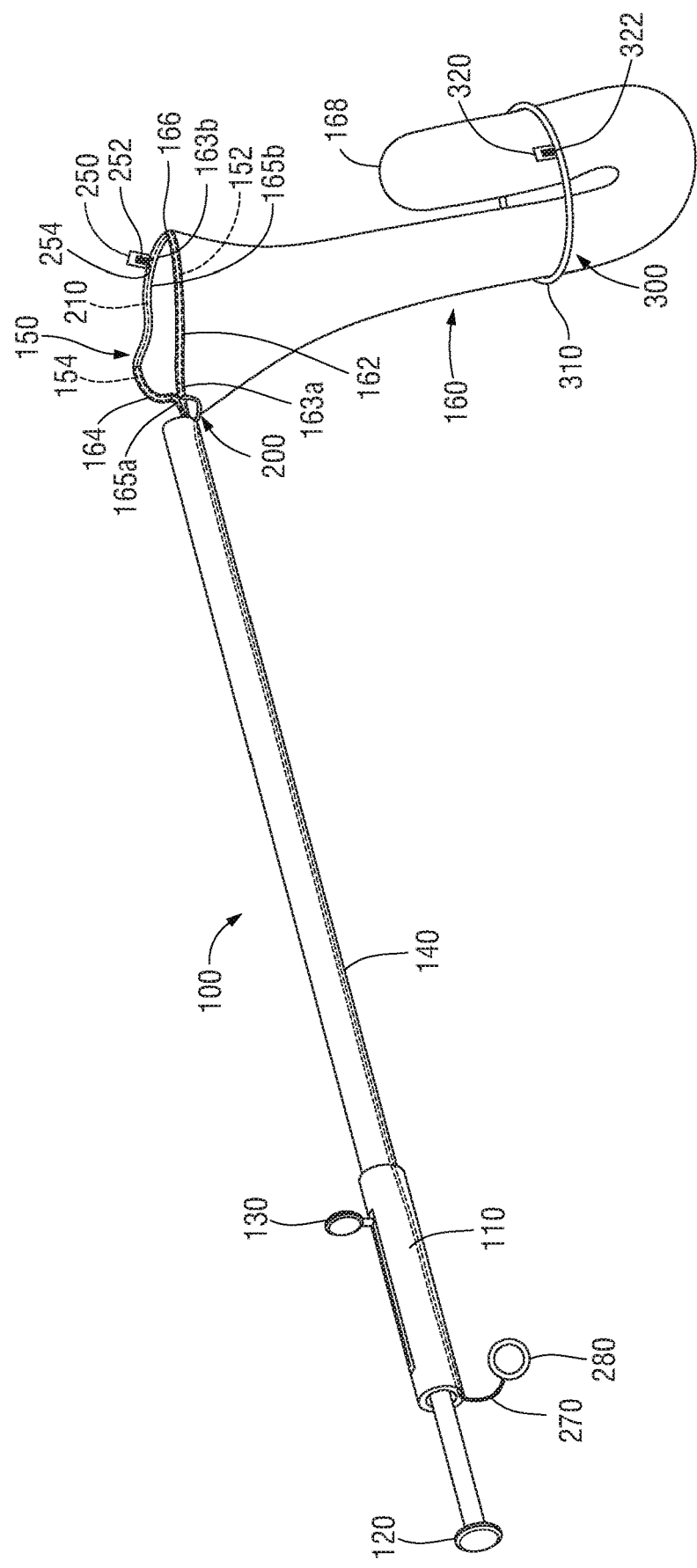
FIG. 2 is a side, perspective view of the tissue specimen retrieval device of FIG. 1, wherein the end effector assembly is disposed in a deployed, aligned position.
Figure 3:
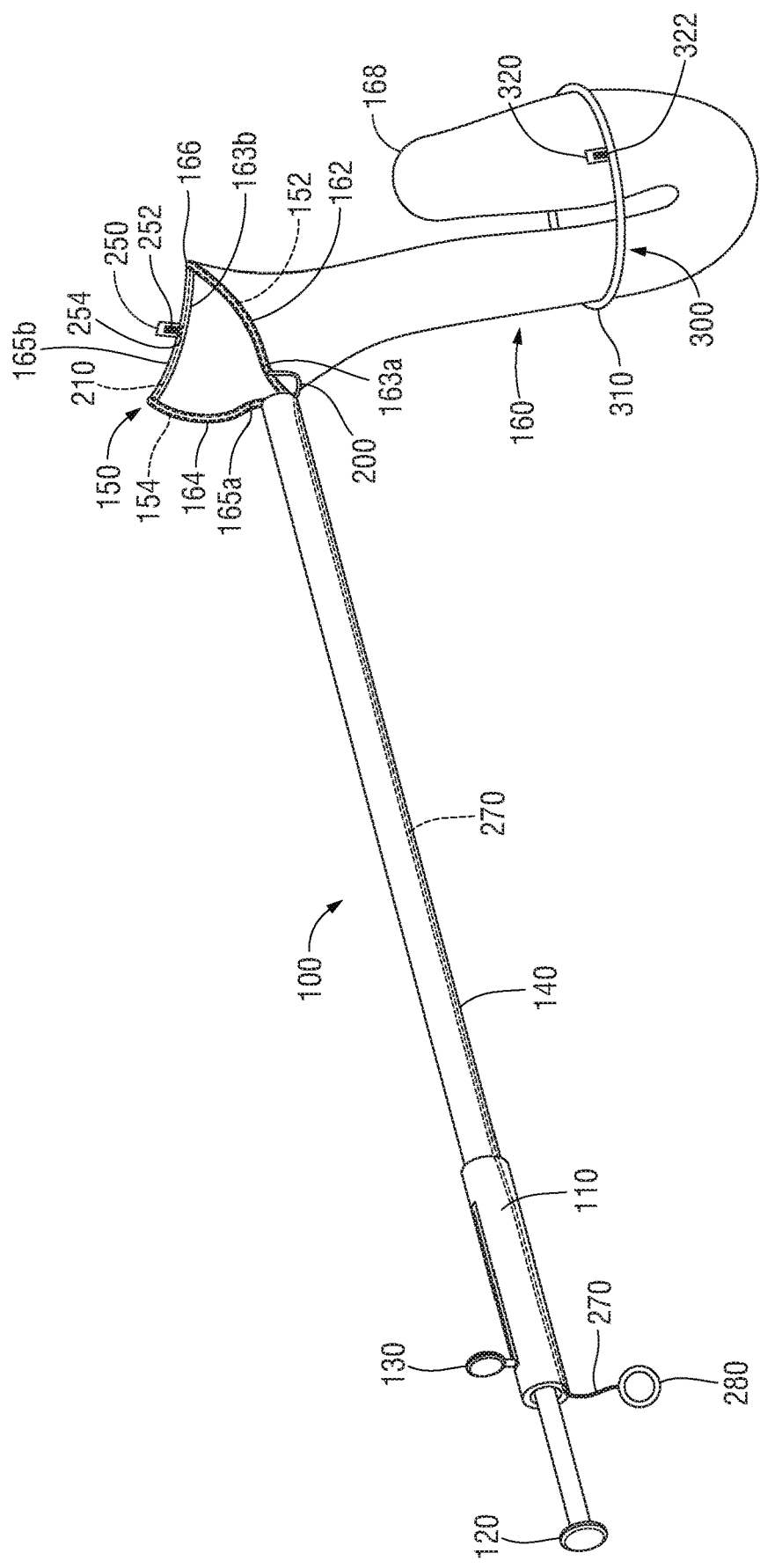
FIG. 3 is a side, perspective view of the tissue specimen retrieval device of FIG. 1, wherein the end effector assembly is disposed in a deployed, articulated position.

Turning to FIGS. 1-3, a tissue specimen retrieval device provided in accordance with the present disclosure is shown generally identified by reference numeral 100. Tissue specimen retrieval device 100 includes a housing 110, first and second actuators 120, 130 operably associated with housing 110, an outer shaft 140 extending distally from housing 110, an end effector assembly 150 selectively deployable from the distal end of outer shaft 140, a tissue specimen bag 160 releasably supported on end effector assembly 150, and an articulation mechanism 180 (FIG. 4) configured to enable selective articulation of end effector assembly 150 relative to outer shaft 140 in the deployed position of end effector assembly 150. Tissue specimen retrieval device 100 further includes a cinch assembly 200, as detailed below, that, in embodiments, includes a distal cinch tab 250. Tissue specimen retrieval device 100 may additionally or alternatively include, as also detailed below, a slack ring 300. Slack ring 300, in embodiments where provided, may be incorporated into tissue specimen retrieval device 100 during manufacturing or may be attachable by the end-user before us or during use (externally of the internal surgical site or within the internal surgical site).

Housing 110, although illustrated as defining a generally tubular configuration, may define any suitable configuration to facilitate grasping and manipulating tissue specimen retrieval device 100 such as, for example, a pencil-grip configuration, a pistol-grip configuration, etc., and may include any suitable features to enhance ergonomics such as, for example, recesses, protrusions, textured surfaces, finger rings, etc.

First actuator 120 is operably associated with housing 110 and coupled to end effector assembly 150 to enable selective extension and retraction of end effector assembly 150 relative to outer shaft 140 between a retracted position (FIG. 1) and a deployed position (FIG. 2) in response to actuation of first actuator 120. Alternatively, first actuator 120 may be coupled to outer shaft 140 to enable selective extension and retraction of outer shaft 140 relative to end effector assembly 150 to similarly move end effector assembly 150 between the retracted position (FIG. 1) and the deployed position (FIG. 2) relative to outer shaft 140. First actuator 120 may be configured a plunger actuator that is selectively manipulatable relative to housing 110 along a longitudinal axis of housing 110, as illustrated, or may define any other suitable configuration such as, for example, a sliding actuator slidable along housing 110, a pivoting actuator pivotable relative to housing 110, etc.

Second actuator 130 is operably associated with housing 110 and coupled to articulation mechanism 180 (FIG. 4) to enable selective articulation of end effector assembly 150 relative to outer shaft 140, once deployed from outer shaft 140, between an aligned position (FIG. 2) and an articulated position (FIG. 3), in response to actuation of second actuator 130. Second actuator 130 may be configured as a sliding actuator slidable along housing 110, as illustrated, or may define any other suitable configuration such as, for example, a pivoting actuator pivotable relative to housing 110, a plunger actuator that is selectively manipulatable relative to housing 110 along a longitudinal axis of housing 110, etc.

Continuing with reference to FIGS. 1-3, outer shaft 140 extends distally from housing 110 and is configured for insertion through an abdominal access cannula "AC" (FIGS. 4 and 5), a vaginal access cannula "VC" (FIG. 7), or a suitable passageway, naturally occurring or surgically created, without use of a cannula, into an internal body cavity "B" (FIGS. 4-7). Outer shaft 140 may be substantially rigid (within manufacturing tolerances and in response to reasonable loads applied thereto) or may include one or more portions configured to flex and/or articulate relative to a longitudinal axis thereof. Outer shaft 140, as noted above, is fixed relative to housing 110 and end effector assembly 150 is movable relative to outer shaft 140 and housing 110 to enable selective deployment of end effector assembly 150 from outer shaft 140. As an alternative to having outer shaft 140 fixed relative to housing 110 and end effector assembly 150 movable relative thereto to deploy end effector assembly 150, outer shaft 140 may be movable relative to housing 110 and end effector assembly 150. In either configuration, in response to actuation of first actuator 120, e.g., from an un-actuated position (FIG. 1) to an actuated position (FIGS. 2-3), end effector 150 is moved from the retracted position (see FIG. 1), wherein end effector assembly 150 is disposed within outer shaft 140, to the deployed position (FIGS. 2-3), wherein end effector assembly 150 extends distally from outer shaft 140.

End effector assembly 150 includes a pair of arms 152, 154 and, as noted above, releasably supports tissue specimen bag 160 thereon. More specifically, tissue specimen bag 160 depends from arms 152, 154. Arms 152, 154 are configured for positioning within one or more channels 162, 164 formed about at least a portion of open end 166 of tissue specimen bag 160 to retain tissue specimen bag 160 on arms 152, 154. In the retracted position of end effector assembly 150, arms 152, 154 may be resiliently flexed inwardly to enable accommodation of arms 152, 154 within outer shaft 140. Tissue specimen bag 160 may be furled, folded, or otherwise positioned in the retracted position of end effector assembly 150 to enable accommodation of tissue specimen bag 160 within outer shaft 140. Upon deployment of end effector assembly 150 from outer shaft 140, arms 152, 154 are configured to resiliently return to a spaced-apart, curved configuration for retaining tissue specimen bag 160 thereon in an open condition, thus enabling insertion of a tissue specimen "T" (FIGS. 4-7) through open end 166 of tissue specimen bag 160 and into the interior thereof. The resilient return of arms 152, 154 may also serve to unfold, unfurl, or otherwise manipulate tissue specimen bag 160 upon deployment from outer shaft 140.

Referring to FIGS. 2 and 3, tissue specimen bag 160 may be formed from any suitable bio-compatible material (or materials), e.g., ripstop nylon, configured to retain a tissue specimen "T" (FIGS. 4-7) therein. As noted above, tissue specimen bag 160 depends from arms 152, 154 of end effector assembly 150 in the deployed position of end effector assembly 150 such that articulation of arms 152, 154 likewise articulates tissue specimen bag 160.

Tissue specimen bag 160 defines at least one opening, e.g., at open end 166 thereof, and includes first and second channels 162, 164 formed about open end 166 thereof for receipt of arms 152, 154, respectively, therein. First and second channels 162, 164 each extend about approximately half the circumference of open end 166 of tissue specimen bag 160 with the proximal ends 163a, 165a of channels 162, 164, respectively, opposing and spaced-apart from one another and the distal ends 163b, 165b of channels 162, 164, respectively, opposing and spaced-apart from one another. The proximal ends 163a, 165a of channels 162, 164, respectively, permit insertion of arms 152, 154 therethrough and into channels 162, 164, respectively, to retain tissue specimen bag 160 on end effector assembly 150 and also permit withdrawal of arms 152, 154 from channels 162, 164 to disengaged tissue specimen bag 160 from end effector assembly 150. Distal ends 163b, 165b of channels 162, 164, respectively, are spaced-apart to expose distal cinch tab 250 of cinch assembly 200 therebetween and enable distal cinch tab 250 to extend from open end 166 of tissue specimen bag 160. Cinch loop 210 of cinch assembly 200 also extends through channels 162, 164 about the circumference of open end 166 of tissue specimen bag 160 and support distal cinch tab 250 thereon. However, as opposed to sharing channels 162, 164, tissue specimen bag 160 may alternatively include separate channels for arms 152, 154 of end effector assembly 160 and cinch loop 210. Cinch assembly 200 is detailed below.

Tissue specimen bag 160, in embodiments, defines an elongated configuration extending between open end 166 and a closed end 168 thereof, although tissue specimen bag 160 may alternatively have two or more open ends and/or may define any other suitable configuration. An elongated configuration of tissue specimen bag 160 enables the open end 166 of tissue specimen bag 160, once a tissue specimen "T" (FIGS. 4-7) is loaded therethrough and into tissue specimen bag 160, to be exteriorized to facilitate tissue breakdown and removal in an enclosed environment (see FIG. 6). However, the additional material of tissue specimen bag 160 which provides the elongated configuration may interfere with manipulation of end effector assembly 150 and tissue specimen bag 160, loading of a tissue specimen into tissue specimen bag 160, and/or visualization within the internal surgical site. As such, slack ring 300 may be provided to help contain the material of specimen tissue bag 160, as detailed below.

Figure 4:
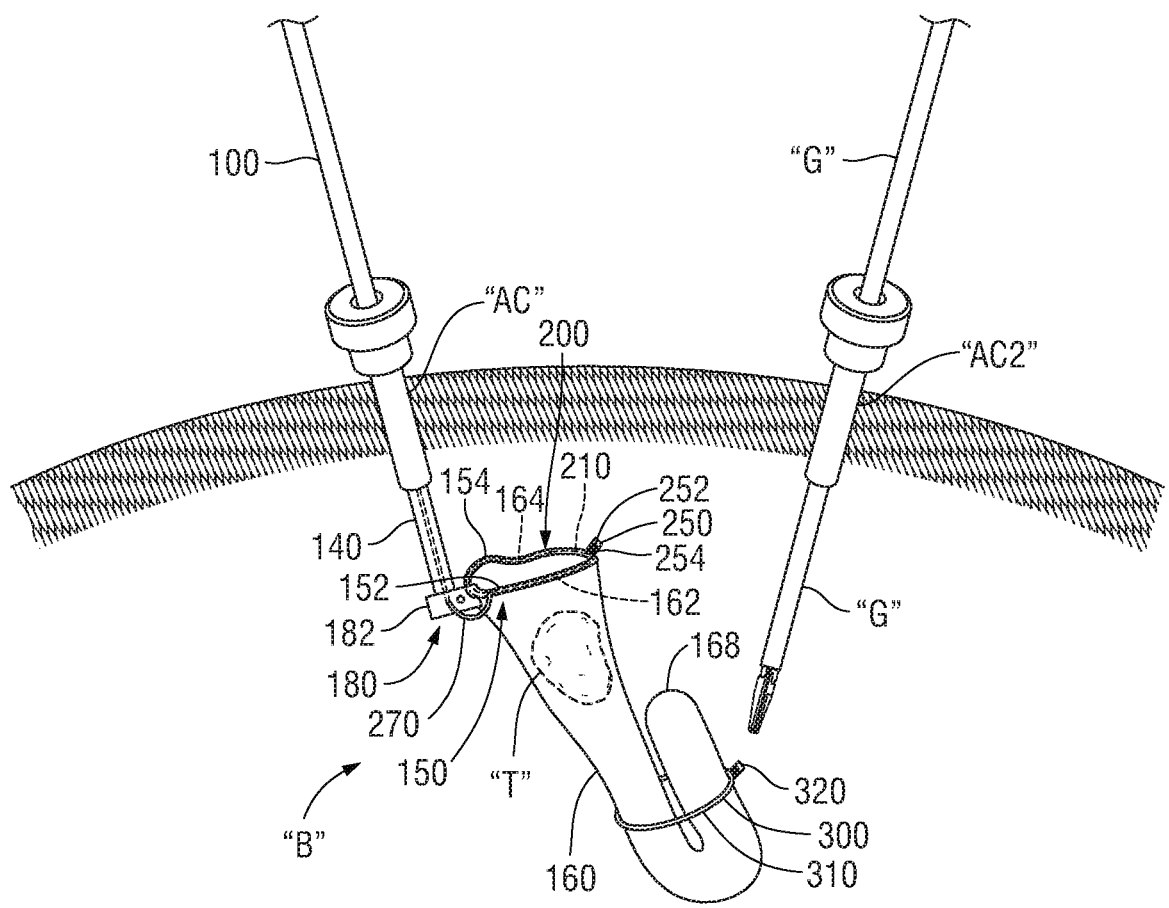
FIG. 4 is a perspective view of the tissue specimen retrieval device of FIG. 1 inserted through an abdominal access cannula into an internal body cavity with a tissue specimen disposed within the specimen bag and a slack ring engaged about the specimen bag.

Continuing with reference to FIGS. 2 and 3, and additionally to FIG. 4, articulation mechanism 180 operably couples second actuator 130 with arms 152, 154 of end effector assembly 150 to enable selective articulation of end effector assembly 150 and, thus, tissue specimen bag 160, relative to outer shaft 140 when end effector assembly 150 is disposed in the deployed position. Articulation mechanism 180 may include, for example, an articulation block 182 supporting the proximal ends of arms 152, 154 of end effector assembly 150 thereon such that rotation of articulation block 182 relative to outer shaft 140 articulates arms 152, 154 relative to outer shaft 140. Any suitable translational, rotational, pivoting, camming, etc. actuation member (not shown) of articulation mechanism 180 and/or any other suitable drive components (not shown), e.g., gears, pin-slot engagements, springs, etc., of articulation mechanism 180 operably couple articulation block 182 with second actuator 130 such that actuation of second actuator 130 rotates articulation block 182 to thereby articulate arms 152, 154 of end effector assembly 150 relative to outer shaft 140. Other suitable articulation mechanisms are also contemplated. Alternatively, in embodiments, articulation mechanism 180 is omitted.

Referring again to FIGS. 2-3, cinch assembly 200 includes a cinch loop 210, a distal cinch tab 250, an elongated tether 270, and a proximal finger ring 280. Cinch loop 210, as noted above, extends through channels 162, 164 of tissue specimen bag 160 about the circumference of open end 166 of tissue specimen bag 160. Elongated tether 270 is operably coupled to tissue specimen bag 160 and/or cinch loop 210 and extends proximally from cinch loop 210 through outer shaft 140 and housing 110 to proximal finger ring 280, which is secured to the proximal end of elongated tether 270. In embodiments, elongated tether 270 and cinch loop 210 may be coupled to one another via a slip knot (not shown) or other suitable configuration such that proximal translation of elongated tether 270 relative to tissue specimen bag 160 constricts cinch loop 210 about open end 166 of tissue specimen bag 160 to close open end 166 of tissue specimen bag 160. Proximal finger ring 280 facilitates pulling of elongated tether 270 proximally.

Elongated tether 270 may additionally or alternatively be utilized to maintain tissue specimen bag 160 about arms 152, 154 of end effector assembly 150 such as, for example, by grasping or otherwise securing proximal finger ring 280 to ensure tissue specimen bag 160 does not slide off of end effector assembly 150 during extension, retraction, or manipulation thereof. In such a configuration, elongated tether 270 may be coupled to tissue specimen bag 160 and may enable repeated extension/retraction of end effector assembly 150 to/from outer shaft 140 without disengaging tissue specimen bag 160 therefrom. When it is desired to release tissue specimen bag 160 from end effector assembly 150, elongated tether 270 may be cut or proximal finger ring 280 otherwise removed from elongated tether 270 to enable proximal withdrawal of tissue specimen retrieval device 100 with elongated tether 270 and tissue specimen bag 160 left behind and/or distal removal of tissue specimen bag 160 and elongated tether 270 from engagement with tissue specimen retrieval device 100. In embodiments, separate elongated tethers 270 for cinching tissue specimen bag 160 closed and retaining tissue specimen bag 160 on end effector assembly 150 are provided.

Figure 5:
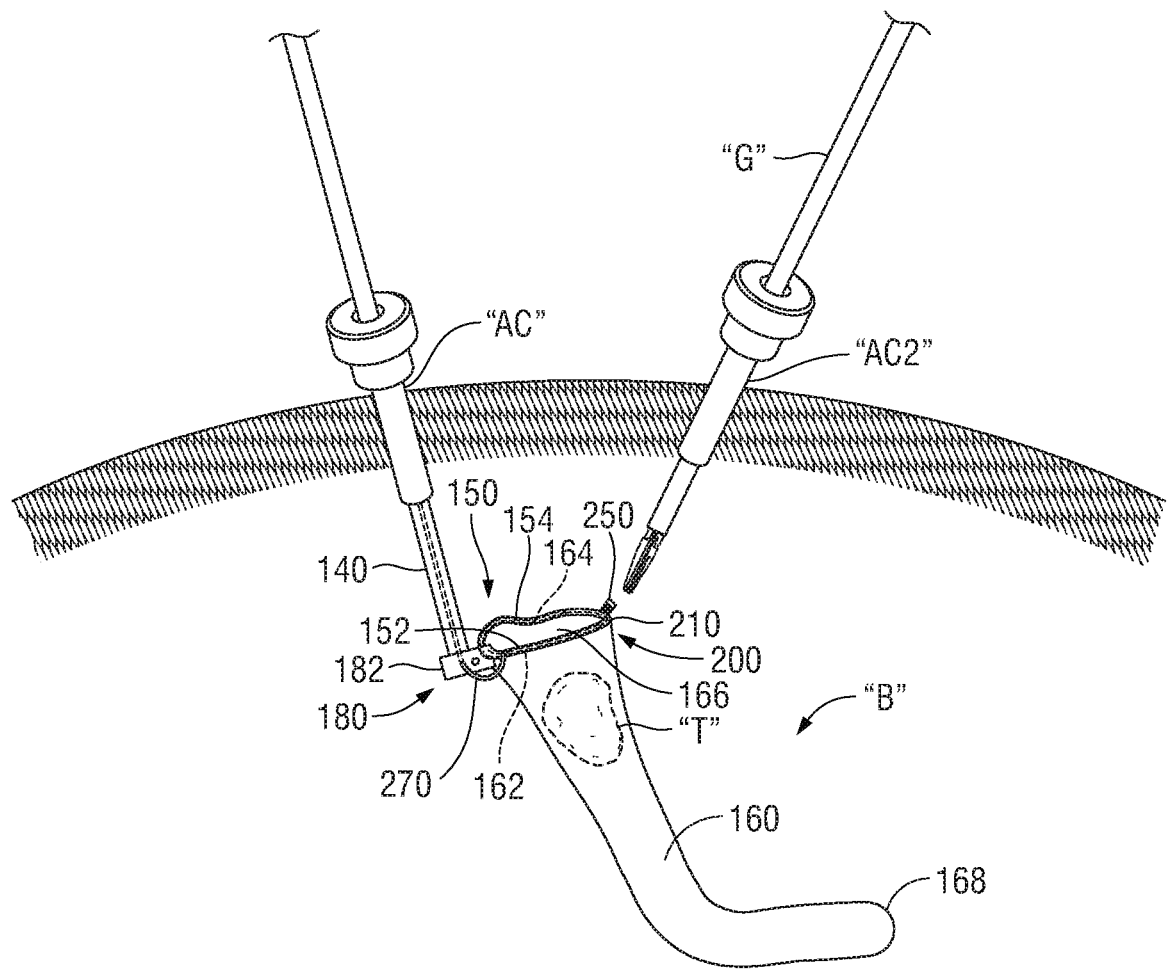
FIG. 5 is a perspective view of the tissue specimen retrieval device of FIG. 1 inserted through the abdominal access cannula into the internal body cavity with the tissue specimen disposed within the specimen bag and the slack ring removed.

Distal cinch tab 250, as noted above, is engaged with cinch loop 210 and disposed between distal ends 163b, 165b of channels 162, 164, respectively, of tissue specimen bag 160. Distal cinch tab 250 extends from cinch loop 210 and tissue specimen bag 160 such that distal cinch tab 250 is presented for grasping using a suitable instrument, e.g., a surgical grasper "G" (FIG. 5). To this end, distal cinch tab 250 may include an aperture 252 and/or other suitable grasping features(s) to facilitate grasping distal cinch tab 250 with a suitable surgical instrument such as surgical grasper "G" (FIG. 5). Distal cinch tab 250 and cinch loop 210 may be coupled to one another via a slip knot 254 or other suitable configuration such that distal pulling of distal cinch tab 250 relative to tissue specimen bag 160 constricts cinch loop 210 about open end 166 of tissue specimen bag 160 to close open end 166 of tissue specimen bag 160. Alternatively, distal cinch tab 250 may be fixedly engaged with cinch loop and open end 166 of tissue specimen bag 160 may be closed by maintaining tissue specimen bag 160 in position (e.g., via grasping or securing elongated tether 270) and pulling distal cinch tab 250 relative to tissue specimen bag 160.

Continuing with reference to FIGS. 2-3, slack ring 300, as noted above, helps contain the material of specimen tissue bag 160. Slack ring 300, more specifically, includes a ring body 310, e.g., a resiliently flexible O-ring, and a grasping tab 320 supported by and extending from ring body 310. Ring body 310 is configured for positioning about multiple layers of tissue specimen bag 160 to take up the slack of tissue specimen bag 160. More specifically, tissue specimen bag 160 is configured to be folded back upon itself one or more times and, thereafter, ring body 310 positioned about the folded layers of tissue specimen bag 160. Ring body 310 may be resiliently expanded for positioning about the folded layers of tissue specimen bag 160 such that ring body 160 is retained about the folded layers of tissue specimen bag 160 under its bias. As noted above, slack ring 300 may be installed during manufacturing or by the end-user before loading tissue specimen bag 160 into outer shaft 140, or may be attached to the folded layers of tissue specimen bag 160 by the end-user within the internal surgical site after deployment of tissue specimen bag 160.

Grasping tab 320 extends from ring body 310 such that grasping tab 320 is presented for grasping using a suitable instrument, e.g., a surgical grasper "G" (FIG. 4). To this end, grasping tab 320 may include an aperture 322 and/or other suitable grasping features(s) to facilitate grasping of grasping tab 320 with a suitable surgical instrument such as surgical grasper "G" (FIG. 4). Once grasping tab 320 is grasped, slack ring 300 may be manipulated to slide slack ring 300 off of tissue specimen bag 160, thus letting tissue specimen bag 160 fully unfurl. As an alternative to pulling slack ring 300 to slide off of tissue specimen bag 160, grasping tab 320 may be coupled to a tear-away feature (not shown) or other suitable releasable engagement feature associated with ring body 310 such that, upon pulling of grasping tab 320, ring body 310 is opened, thus enabling passage of tissue specimen bag 160 through the open mouth of ring body 310 to remove slack ring 300 from about tissue specimen bag 160.

Figure 6:
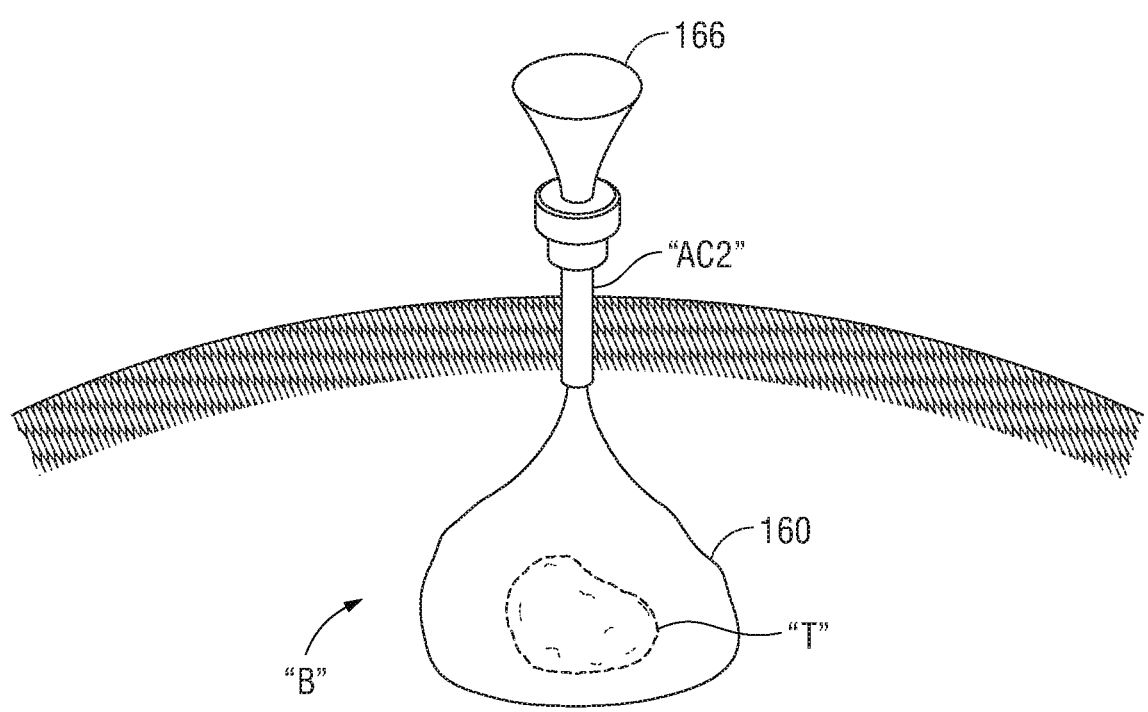
FIG. 6 is a perspective view of the tissue specimen bag of the tissue specimen retrieval device of FIG. 1 including the tissue specimen disposed therein, wherein an open end of the tissue specimen bag is exteriorized through an abdominal access cannula.

Turning now to FIGS. 4-6, in conjunction with FIGS. 1-3, the use and operation of the tissue specimen retrieval device 100 is detailed. Initially, end effector assembly 150 is disposed in the retracted position (FIG. 1) to facilitate insertion of tissue specimen retrieval device 100 through an abdominal access cannula "AC" or natural passageway into an internal body cavity "B."

Once tissue specimen retrieval device 100 is disposed within the internal body cavity "B" as desired, end effector assembly 150 is deployed from outer shaft 140 by actuating first and second actuators 120, 130 relative to housing 110 from more-distal positions to more-proximal positions to thereby advance end effector assembly 150 from outer shaft 140 such that end effector assembly 150 and tissue specimen bag 160 are deployed to the deployed position. At this point, end effector assembly 150 remains aligned on the longitudinal axis of outer shaft 140.

If it is desired to articulate end effector assembly 150 relative to outer shaft 140 after end effector assembly 150 is deployed from outer shaft 140, second actuator 130 is moved proximally from the more-distal position relative to housing 110 to a suitable proximal position to thereby rotate articulation block 182, thereby articulating end effector assembly 150 relative to outer shaft 140 a desired amount.

With particular reference to FIG. 4, at this point, slack ring 300, if pre-loaded on tissue specimen bag 160, remains disposed about the folded layers of tissue specimen bag 160. If not pre-loaded, slack ring 300 may now be positioned about tissue specimen bag 160. As such, with tissue specimen bag 160 in a more neatly-organized condition, manipulation of tissue specimen bag 160 and visualization thereto to enable insertion of a tissue specimen "T" through open end 166 of tissue specimen bag 160 and into tissue specimen bag 160 is facilitated. Once the tissue specimen "T" is deposited into tissue specimen bag 160, a surgical grasper "G," for example, may be inserted through a second abdominal access cannula "AC2" or other cannula or passageway into the internal body cavity "B" to grasp grasping tab 320 of slack ring 300 to remove slack ring 300 from about tissue specimen bag 160 and withdrawn slack ring 300 from the internal body cavity "B," thus permitting tissue specimen bag 160 to fully unfurl within the internal body cavity "B."

Turning to FIG. 5, with tissue specimen bag 160 fully unfurled within the internal body cavity "B" and the tissue specimen "T" disposed therein, tissue specimen bag 160 may be removed from end effector assembly 150 and open end 166 cinched closed to enable open end 166 of tissue specimen bag 160 to be exteriorized such as, for example, through the second abdominal access cannula "AC2." In order to cinch closed open end 166 of tissue specimen bag 160 and remove tissue specimen bag 160 from end effector assembly 150, surgical grasper "G," for example, may be inserted through second abdominal access cannula "AC2" or other cannula or passageway into the internal body cavity "B" to grasp distal cinch tab 250 and pull distal cinch tab 250 in an opposite direction from end effector assembly 150, thus cinching closed cinch loop 210 about open end 166 of tissue specimen bag 160 and pulling tissue specimen bag 160 off of end effector assembly 150.

In order to ensure open end 166 of tissue specimen bag 160 is properly cinched closed, in embodiments, proximal finger ring 280 (FIGS. 2-3) is grasped or otherwise secured to tension elongated tether 270 (FIGS. 2-3), thereby maintaining tissue specimen bag 160 about end effector assembly 150. Once open end 166 of tissue specimen bag 160 is cinched closed, elongated tether 270 may be cut or otherwise disengaged from proximal finger ring 280 (FIGS. 2-3) to enable removal of tissue specimen bag 160 from end effector assembly 150 and withdrawal of tissue specimen retrieval device 100. Prior to withdrawal of tissue specimen retrieval device 100, end effector assembly 150 is returned to the retracted position to facilitate withdrawal of tissue specimen retrieval device 100.

Referring also to FIG. 6, once open end 166 of tissue specimen bag 160 is cinched closed and tissue specimen bag 160 removed from end effector assembly 150, distal cinch tab 250 may be exteriorized to thereby exteriorize open end 166 of tissue specimen bag 160 by, for example, pulling surgical grasper "G," grasping distal cinch tab 250, through second abdominal access cannula "AC2" tot hereby pull distal cinch tab 250 and open end 166 of tissue specimen bag 160 through second abdominal access cannula "AC2." Once exteriorized, open end 166 of tissue specimen bag 160 may be re-opened to enable breakdown of the tissue specimen "T" within the enclosed environment within tissue specimen bag 160 to facilitate removal of the tissue specimen "T" through second abdominal access cannula "AC2." Ultimately, the remainder of tissue specimen bag 160 may likewise be removed through second abdominal access cannula "AC2."

Figure 7:
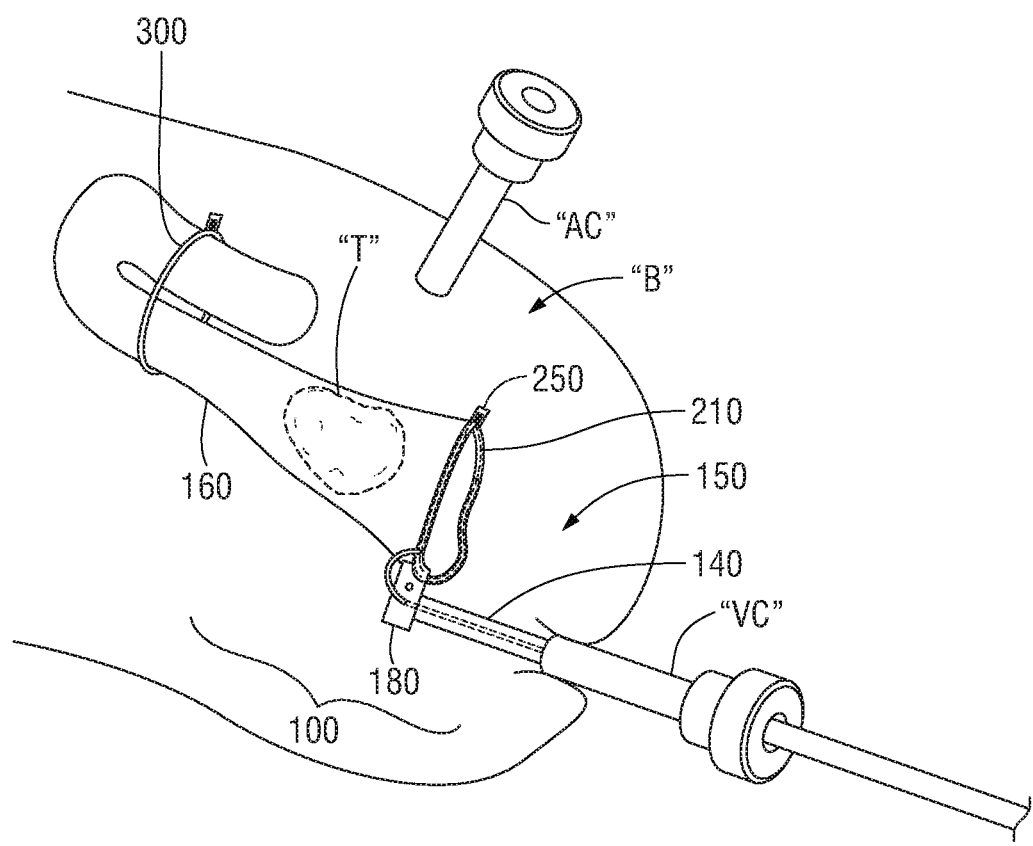
FIG. 7 is a perspective view of the tissue specimen retrieval device of FIG. 1 inserted through a vaginal access cannula into an internal body cavity.

Turning to FIG. 7, as an alternative to the above abdominal-based approach using first and second abdominal access cannulas "AC" and "AC2," a vaginal access cannula "VC" may be utilized to enable insertion of surgical tissue retrieval device 100 and/or surgical grasper "G" therethrough, or vaginal access to the interior body cavity "B" may be provided without the use of a cannula. Any suitable combination of abdominal, vaginal, and/or other surgically created or naturally occurring passageways may be utilized to provide a desired approach angle or desired combination of approach angles to facilitate removal of a tissue specimen "T" from the internal body cavity "B" using tissue specimen retrieval device 100.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
a housing;
an outer shaft extending distally from the housing;
an end effector assembly extending distally from the outer shaft in a deployed position thereof, the end effector assembly defining a proximal end portion positioned adjacent a distal end portion of the outer shaft in the deployed position and a distal end portion distally-spaced from the distal end portion of the outer shaft in the deployed position;
a tissue specimen bag supported on the end effector assembly, the tissue specimen bag including an open end extending between the proximal and distal end portions of the end effector assembly;
a cinch loop disposed about the open end of the tissue specimen bag; and
a distal cinch tab disposed at the distal end portion of the end effector assembly and extending from the open end of the tissue specimen bag, the distal cinch tab operably coupled to the cinch loop such that pulling the distal cinch tab distally relative to the cinch loop constricts the cinch loop about the open end of the tissue specimen bag to cinch the open end of the tissue specimen bag closed.

2. The tissue specimen retrieval device according to claim 1, wherein the distal cinch tab is operably coupled to the cinch loop via a slip knot.

3. The tissue specimen retrieval device according to claim 1, further comprising an elongated tether coupled to the tissue specimen bag towards the proximal end portion of the end effector assembly.

4. The tissue specimen retrieval device according to claim 3, wherein the elongated tether extends proximally through outer shaft and housing to a finger ring.

5. The tissue specimen retrieval device according to claim 1, wherein the end effector assembly is selectively deployable relative to the outer shaft from a retracted position, wherein the end effector assembly is disposed within the outer shaft, to the deployed position.

6. The tissue specimen retrieval device according to claim 1, further comprising an articulation mechanism operably associated with the end effector assembly and configured to articulate the end effector assembly relative to the outer shaft.

7. The tissue specimen retrieval device according to claim 1, wherein the tissue specimen bag defines first and second channels each extending about a portion of the circumference of the open end of the tissue specimen bag.

8. The tissue specimen retrieval device according to claim 7, wherein the end effector assembly includes first and second arms configured to extend at least partially through the first and second channels, respectively.

9. The tissue specimen retrieval device according to claim 7, wherein distal ends of the first and second channels oppose and are spaced-apart from one another, and wherein the distal cinch tab is disposed between the distal ends of the first and second channels.

10. The tissue specimen retrieval device according to claim 7, wherein the cinch loop extends through the first and second channels.

* * * * *